(12) United States Patent
Caizza

(10) Patent No.: US 7,887,518 B2
(45) Date of Patent: *Feb. 15, 2011

(54) SYRINGE ASSEMBLY INCLUDING REUSE PREVENTION MECHANISM

(75) Inventor: Richard J. Caizza, Vernon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/137,685

(22) Filed: Jun. 12, 2008

(65) Prior Publication Data

US 2009/0030377 A1 Jan. 29, 2009

Related U.S. Application Data

(60) Provisional application No. 60/943,421, filed on Jun. 12, 2007.

(51) Int. Cl.
*A61M 5/315* (2006.01)
*A61M 5/00* (2006.01)

(52) U.S. Cl. ..................... 604/220; 604/110

(58) Field of Classification Search .......... 604/110, 604/192, 195, 218, 220, 228, 207–211
See application file for complete search history.

(56) References Cited

U.S. PATENT DOCUMENTS

| | | | |
|---|---|---|---|
| 4,915,692 A | 4/1990 | Verlier | |
| 4,973,310 A | 11/1990 | Kosinski | |
| 5,047,017 A | 9/1991 | Koska | |
| 5,106,372 A | 4/1992 | Ranford | |
| 5,989,219 A | 11/1999 | Villas et al. | |
| 6,368,306 B1 | 4/2002 | Koska | |
| 6,599,269 B1 | 7/2003 | Lewandowski et al. | |
| 7,331,934 B2 * | 2/2008 | Suresh et al. | 604/110 |
| 7,331,935 B2 * | 2/2008 | Barere | 604/110 |
| 2004/0059294 A1 * | 3/2004 | Pelkey et al. | 604/110 |

(Continued)

FOREIGN PATENT DOCUMENTS

WO  WO-2004/028603 A1  4/2004

(Continued)

OTHER PUBLICATIONS

*PCT International Search Report*—PCT/US2008/066651, (Sep. 8, 2008), 6 pgs.

(Continued)

*Primary Examiner*—Kevin C Sirmons
*Assistant Examiner*—Larry R Wilson
(74) *Attorney, Agent, or Firm*—Diehl Servilla LLC

(57) ABSTRACT

A syringe assembly having passive disabling structure includes a barrel and a plunger rod assembly. The plunger rod assembly includes a plunger rod and a stopper connected by an indexing locking element. The number of strokes of the syringe plunger before the stopper is locked into the barrel rendering the syringe assembly unusable is determined by the number of detents on the plunger rod and stopper which engage the locking mechanism. Upon completion of the final delivery stroke, any attempt to withdraw the plunger rod from the barrel will cause the locking element to engage the barrel and trap the stopper in the barrel preventing further use of the syringe.

21 Claims, 13 Drawing Sheets

U.S. PATENT DOCUMENTS

| | | |
|---|---|---|
| 2005/0027250 A1* | 2/2005 | Suresh et al. ............... 604/110 |
| 2006/0079839 A1* | 4/2006 | Moh et al. .................. 604/110 |
| 2006/0173411 A1* | 8/2006 | Barere ....................... 604/110 |

FOREIGN PATENT DOCUMENTS

| | | |
|---|---|---|
| WO | WO-2005/011782 A1 | 2/2005 |
| WO | WO-2006/068650 A1 | 6/2006 |

OTHER PUBLICATIONS

*PCT Written Opinion*, PCT/US2008/066651, (Sep. 8, 2008), 7 pgs.

* cited by examiner

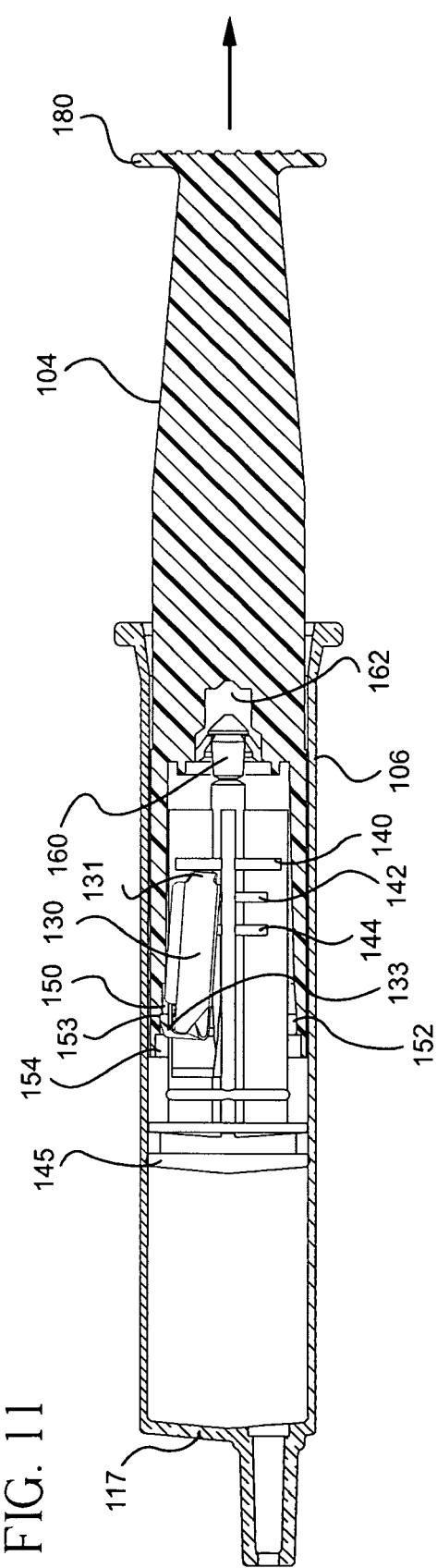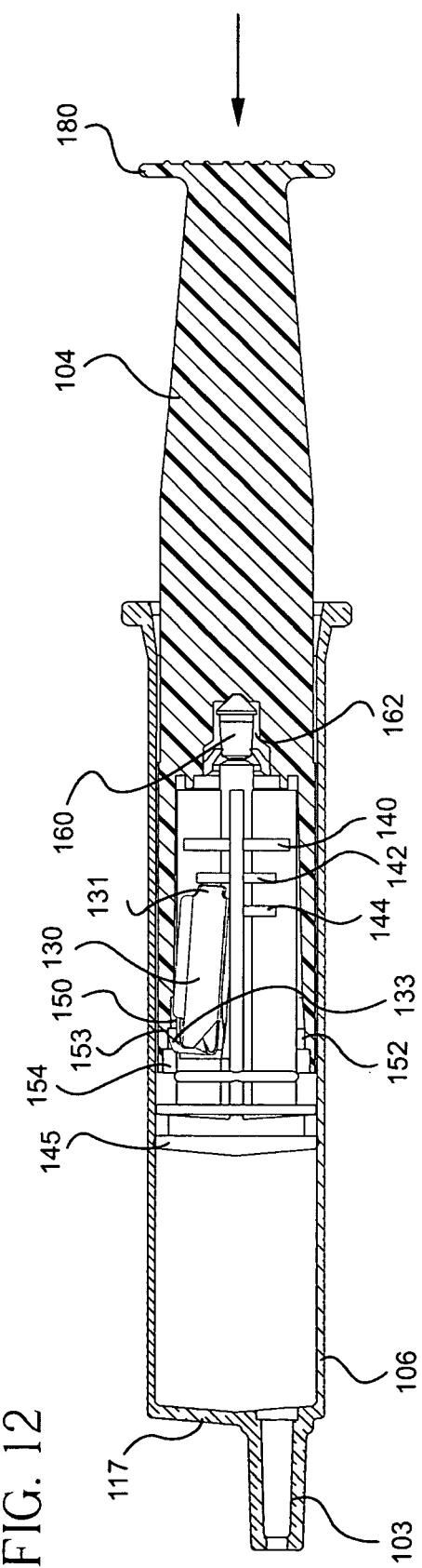

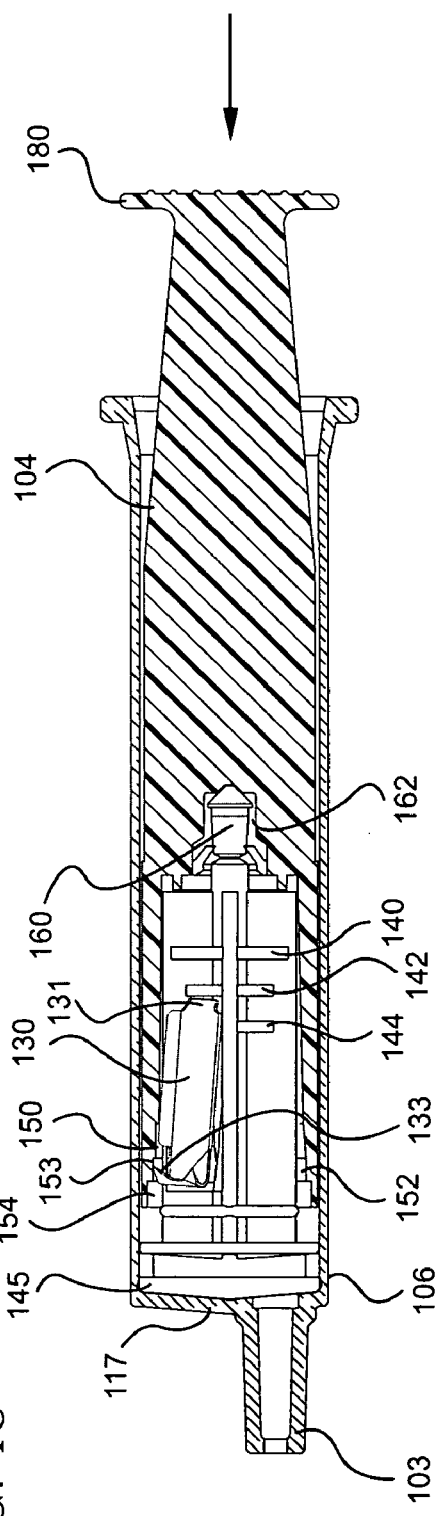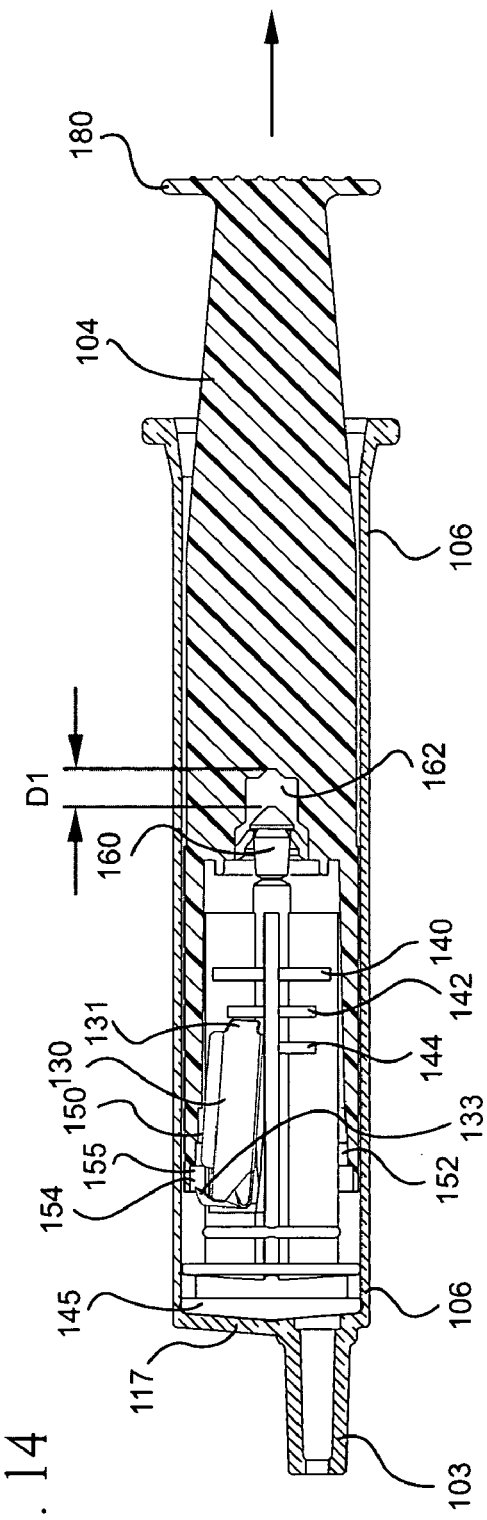
FIG. 13
FIG. 14

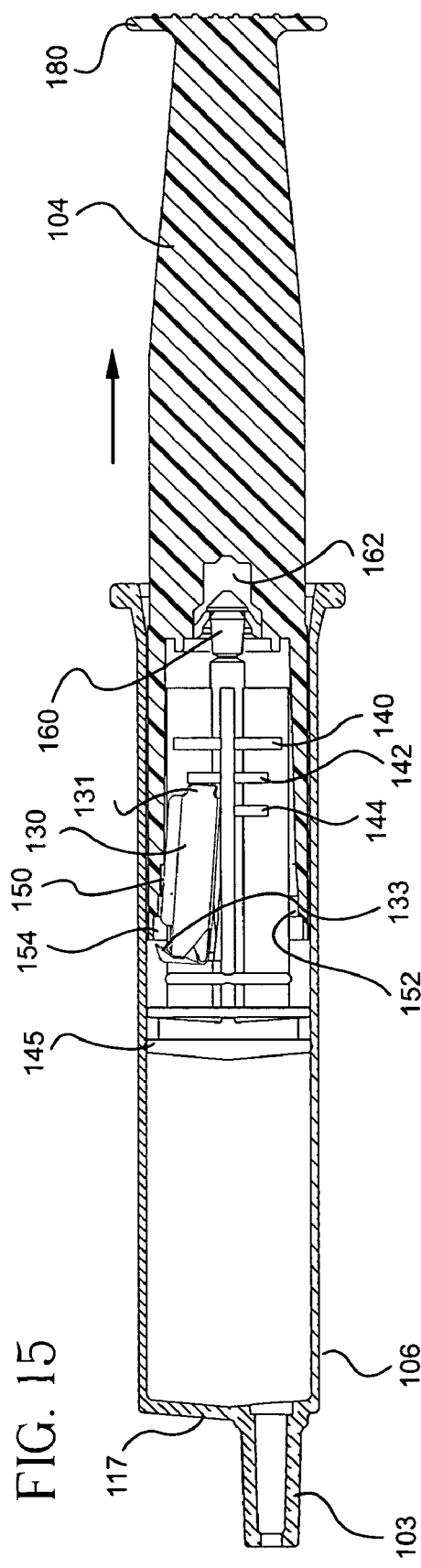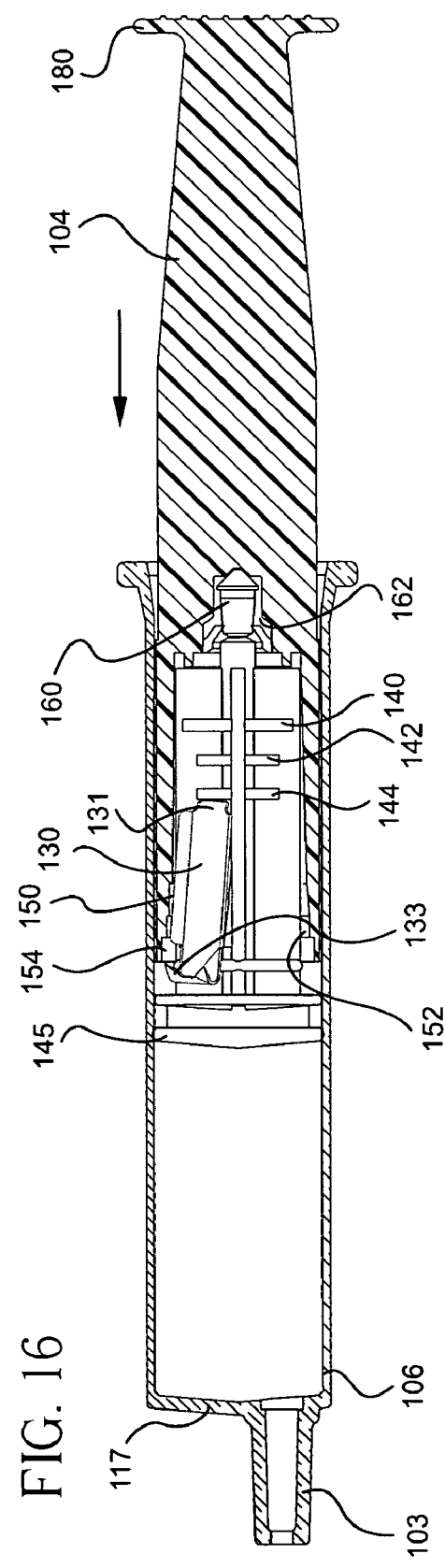

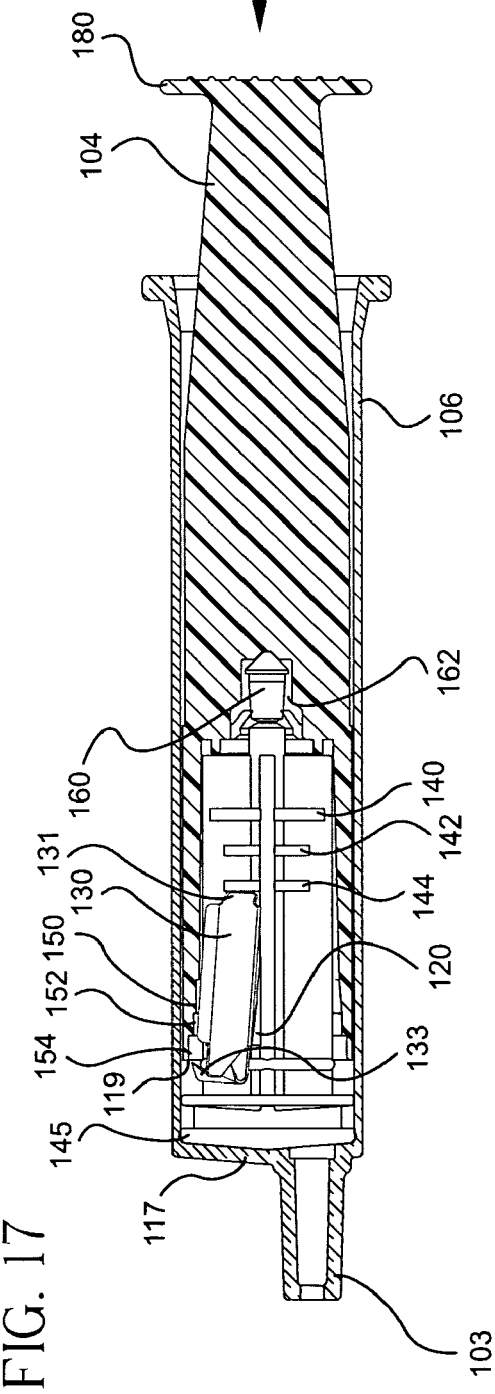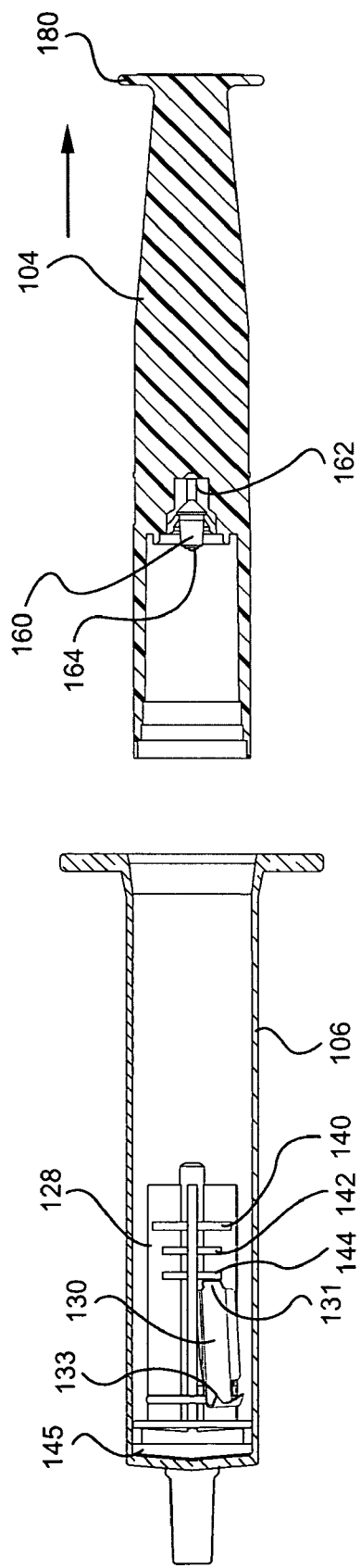
FIG. 17
FIG. 18

SYRINGE ASSEMBLY INCLUDING REUSE PREVENTION MECHANISM

CROSS-REFERENCE TO RELATED APPLICATIONS

This application claims the benefit of priority from U.S. Provisional Application No. 60/943,421, filed Jun. 12, 2007, the disclosure of which is hereby incorporated in its entirety by reference thereto.

TECHNICAL FIELD

The present invention pertains to syringes, and specific embodiments pertain to syringe assemblies having a reuse prevention mechanism.

BACKGROUND

Throughout the world the multiple use of hypodermic syringe products which are intended for single-use only contributes to the transfer of contagious diseases. Intravenous drug users who routinely share and re-use syringes are a high-risk group with respect to the AIDS virus. Also, the effects of multiple use of a single syringe are a major concern in some countries where repeated use of syringe products during mass immunization programs may be responsible for the spread of many diseases.

Many attempts have been made to prevent reuse of syringes. Early efforts have utilized a specific act to destroy the syringe after use either by using a destructive device or by providing a syringe assembly with frangible zones so that the syringe could be rendered inoperable by an application of force. Other attempts have involved including structural elements which would allow the destruction or defeating of the syringe function by a conscious act by the syringe user. Although many of these devices work quite well, they do require the specific intent of the user followed by the actual act to destroy or render the syringe inoperable. These devices are not effective with a user having the specific intent to re-use the hypodermic syringe. Accordingly, there was a need for a single-use hypodermic syringe which, after use, will become inoperable or incapable of further use automatically without any additional act on the part of the user. The automatic function is much harder to provide because the means for rendering the syringe inoperable must not prevent its filling or use under normal conditions.

An example of a single-use syringe which automatically disables after injection is taught in U.S. Pat. No. 4,973,310 to Kosinski. This syringe contains a locking element positioned in the syringe barrel between the plunger rod and the inside surface of the barrel. In use, the syringe allows the user to draw a pre-selected amount of medication into the chamber of the barrel and deliver this medication, as through injection, into the patient. Any attempt to withdraw the plunger to use the syringe a second time will cause the locking element to embed itself into the inside surface of the syringe barrel to prevent proximal motion of the plunger rod.

Despite the availability of single use syringes with disabling mechanisms, there is still a need for improvements to a single-use syringe which will allow a pre-selected number of plunger rod strokes before the automatic disabling mechanism activates. For example, four strokes of the plunger may be required to complete the injection process, when the syringe assembly is used to draw a diluent into the syringe barrel, dispense the diluent into a vial containing the substance to be reconstituted, draw back the reconstituted medication into the syringe and then deliver the contents of the syringe into the patient. It would be desirable to provide such a syringe assembly that is simple and inexpensive to manufacture.

SUMMARY

One embodiment of the invention pertains to a syringe assembly comprising a barrel including a cylindrical side wall having an inside surface defining a chamber for retaining fluid, an open proximal end and a distal end including a distal wall having a passageway therethrough in fluid communication with said chamber; an elongate hollow plunger rod having a proximal end, an open distal end, an interior surface, and a distal lip at the distal end; a stopper at the distal end of the plunger rod, the stopper including a sealing element having a peripheral surface forming a seal with said inside surface of the barrel, and a projection extending proximally from the sealing element and forming a longitudinal recess, at least one distal ramp on the longitudinal recess and at least one proximal recess detent on the longitudinal recess; and a locking element including a proximal portion having a proximal edge and a distal portion having an outwardly facing barb, the locking element positioned in the longitudinal recess so that the barb contacts the interior surface of the plunger rod and the proximal edge contacts the proximal recess detent, wherein proximal sliding movement followed by distal sliding movement of the plunger rod and stopper within the chamber causes the barb to extend past the distal lip on the plunger rod toward the inside surface of the barrel, preventing further distal movement of the plunger rod with respect to the chamber. In one or more embodiments, the stopper longitudinal recess includes a plurality of ramps inclined outwardly in a distal direction and a plurality of proximal recess detents. Distal sliding movement of the plunger rod and stopper causes the distal portion and barbs of the locking element to move outwardly towards the interior surface of the hollow plunger rod.

According to one embodiment, the distal end of the hollow plunger rod includes a plurality of plunger rod ramps complementary to the ramps on the longitudinal recess of the stopper. In a specific embodiment, the assembly further comprises first, second and third proximal recess detents, first, second and third ramps on the longitudinal recess of the stopper and first, second and third plunger rod ramps, the plunger rod ramps providing first, second and third longitudinally spaced barb rests.

In another specific embodiment, the stopper is slidably attached to the distal end of the plunger rod to allow initial relative movement between the plunger rod and the stopper so that the stopper remains stationary when the plunger rod is moved an initiating distance in a proximal direction, causing the barbs on the locking element to move from the first barb rest to the second barb rest. In operation of this specific embodiment, further proximal movement of the plunger rod causes the syringe barrel to be filled with a desired amount of fluid.

Distal movement of the plunger rod after the syringe barrel has been filled results in the stopper remaining in a fixed position so that there is relative movement between the stopper and the plunger rod causing the barbs to advance to the second barb rest and the proximal edge of the locking element to engage the second proximal recess detent while the second ramp on the longitudinal recess of the stopper urges the barbs outwardly to contact the interior surface of the plunger rod.

Further distal movement of the plunger rod causes the seal to contact the distal wall of the barrel until the fluid has been expelled from the barrel.

Still with respect to a specific embodiment, after expulsion of fluid from the syringe, the plunger rod can be moved an initiating distance in a proximal direction during which there is initial relative movement between the plunger rod and the stopper so that the stopper remains stationary, causing the barbs on the locking element to move from the second barb rest to the third barb rest. After this movement, further proximal movement of the plunger rod causes movement of the seal and the plunger rod in a proximal direction while fluid is drawn into the syringe. After fluid is drawn into the syringe, distal movement of the plunger rod results in the stopper remaining in a fixed position so that there is relative movement between the stopper and the plunger rod, causing the barbs to advance to the third barb rest and the proximal edge of the locking element to engage the third proximal recess detent while the third ramp on the longitudinal recess of the stopper urges the barbs outwardly to contact the interior surface of the plunger rod. Thereafter, further distal movement of the plunger rod causes the seal to contact the distal wall of the barrel until the fluid has been expelled from the barrel and the locking element is urged past the distal lip of the plunger rod, causing the barbs to engage the interior wall of the barrel and locking the plunger rod in the barrel.

In one or more embodiments, the proximal end of the stopper includes a frangible connection that breaks upon application of proximal force to the plunger rod after the plunger rod has been locked in the barrel. In specific embodiments, the proximal end of the stopper includes a boss member including the frangible connection. According to an embodiment of the invention, the locking element is made of sheet metal and the stopper is integrally formed of thermoplastic material. In a specific embodiment, the locking element comprises a sheet of material consisting of a single leg.

Another embodiment of the invention pertains to a syringe assembly comprising a barrel including a cylindrical side wall having an inside surface defining a chamber for retaining fluid, an open proximal end and a distal end including a distal wall having a passageway therethrough in fluid communication with said chamber; an elongate hollow plunger rod having a proximal end, an open distal end, an interior surface, and a distal lip on said distal end of said plunger rod, the stopper including a sealing element having a peripheral surface forming a seal with said inside surface of the barrel, and a projection extending proximally from the sealing element and forming a longitudinal recess; and means for locking the plunger rod to the barrel to prevent relative movement of the plunger rod with respect to the barrel after the plunger rod has been moved proximally and then distally for at least one cycle.

Still another embodiment pertains to a syringe assembly comprising a barrel including a cylindrical side wall having an inside surface defining a chamber for retaining fluid, an open proximal end and a distal end including a distal wall having a passageway therethrough in fluid communication with said chamber; an elongate hollow plunger rod having a proximal end, an open distal end, an interior surface, and a distal lip on said distal end of said plunger rod; a stopper at the distal end of the plunger rod, the stopper including a sealing element having a peripheral surface forming a seal with said inside surface of the barrel, and a projection extending proximally from the sealing element and forming a longitudinal recess, first and second distal ramps on the longitudinal recess and first and second detents on the longitudinal recess; and a locking element including a proximal portion having a proximal edge and a distal portion having an outwardly facing point, the locking element positioned in the longitudinal recess so that the distal ramps and the detents on the longitudinal recess cooperate to move the distal portion of the locking element outwardly towards the interior surface of the plunger rod and the proximal edge of the locking element retains the locking element in place, wherein proximal sliding movement followed by distal sliding movement of the plunger rod and stopper within the chamber causes the point to extend past the distal lip on the plunger rod and the inside surface of the barrel, preventing further movement of the plunger rod with respect to the chamber.

BRIEF DESCRIPTION OF THE DRAWINGS

FIG. 11 is an illustration of FIG. 10 after further proximal movement of the plunger rod during a first aspiration stroke;

FIG. 12 is an illustration of FIG. 11 after initial distal movement of the plunger rod;

FIG. 13 is an illustration of FIG. 12 after further distal movement of the plunger rod to expel fluid from the syringe assembly during a first dispensing stroke;

FIG. 14 is an illustration of FIG. 13 after fluid has been expelled from the syringe assembly and initial proximal movement of the plunger rod;

FIG. 15 is a an illustration of FIG. 14 after further proximal movement of the plunger rod to draw fluid into the syringe assembly during a second aspiration stroke;

FIG. 16 is an illustration of FIG. 15 after fluid has been drawn into the syringe assembly and initial distal movement of the plunger rod during a second dispensing stroke;

FIG. 17 is an illustration of FIG. 16 wherein, upon application of further distal force to the plunger rod, the fluid in the syringe assembly has been expelled and the plunger rod has been locked into the barrel of the syringe; and FIG. 18 an illustration of FIG. 17 showing application of proximal force to the plunger rod causing the plunger rod to break away from the stopper according to an embodiment of the invention.

DETAILED DESCRIPTION

Figure 1:
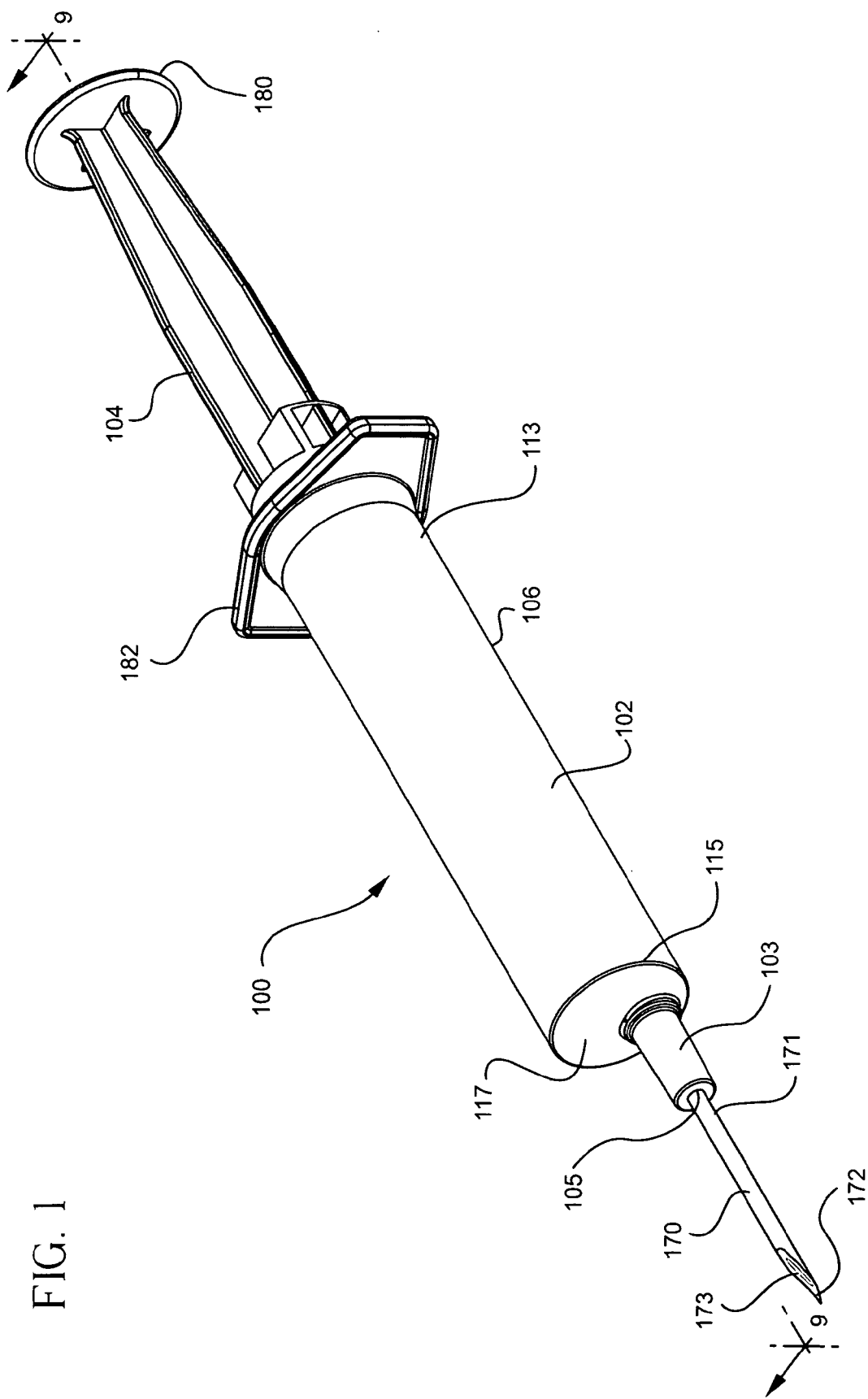
FIG. 1 is a perspective view of a syringe assembly according to an embodiment of the invention.
Figure 2A:
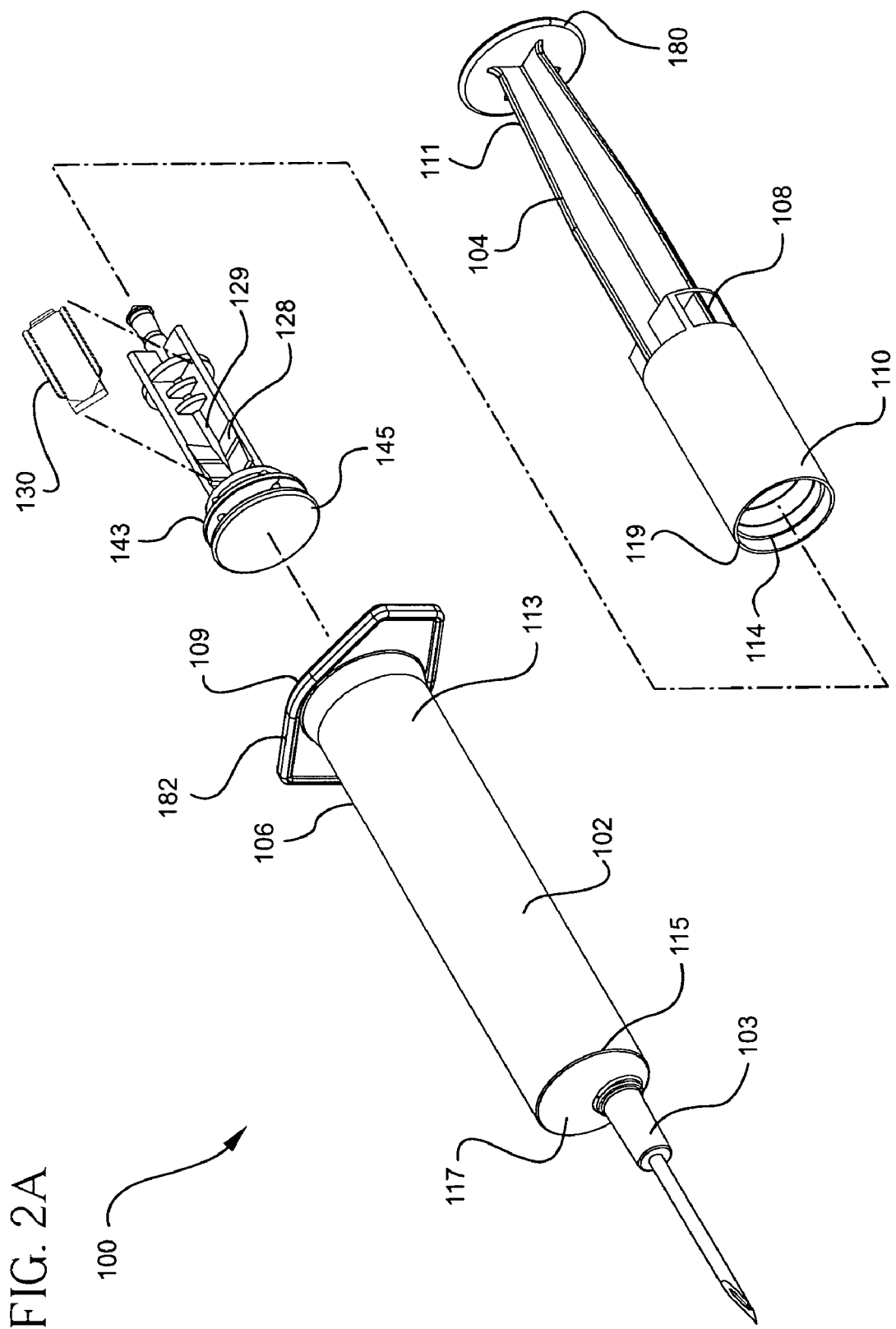
FIG. 2A is an exploded perspective view of the syringe assembly shown in FIG. 1.
Figure 2B:
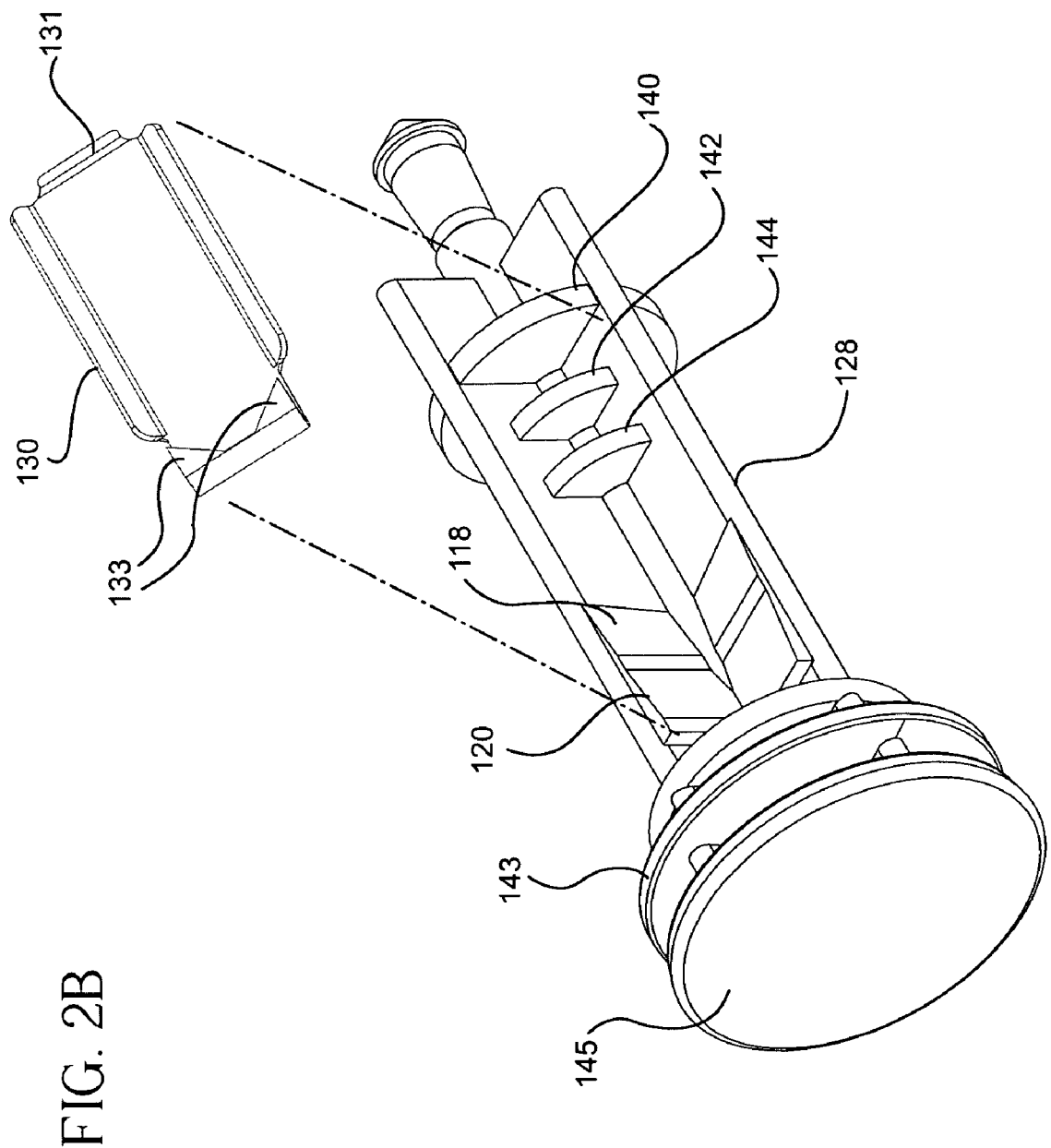
FIG. 2B is an enlarged view of the stopper and locking element shown in FIG. 2A.
Figure 3:
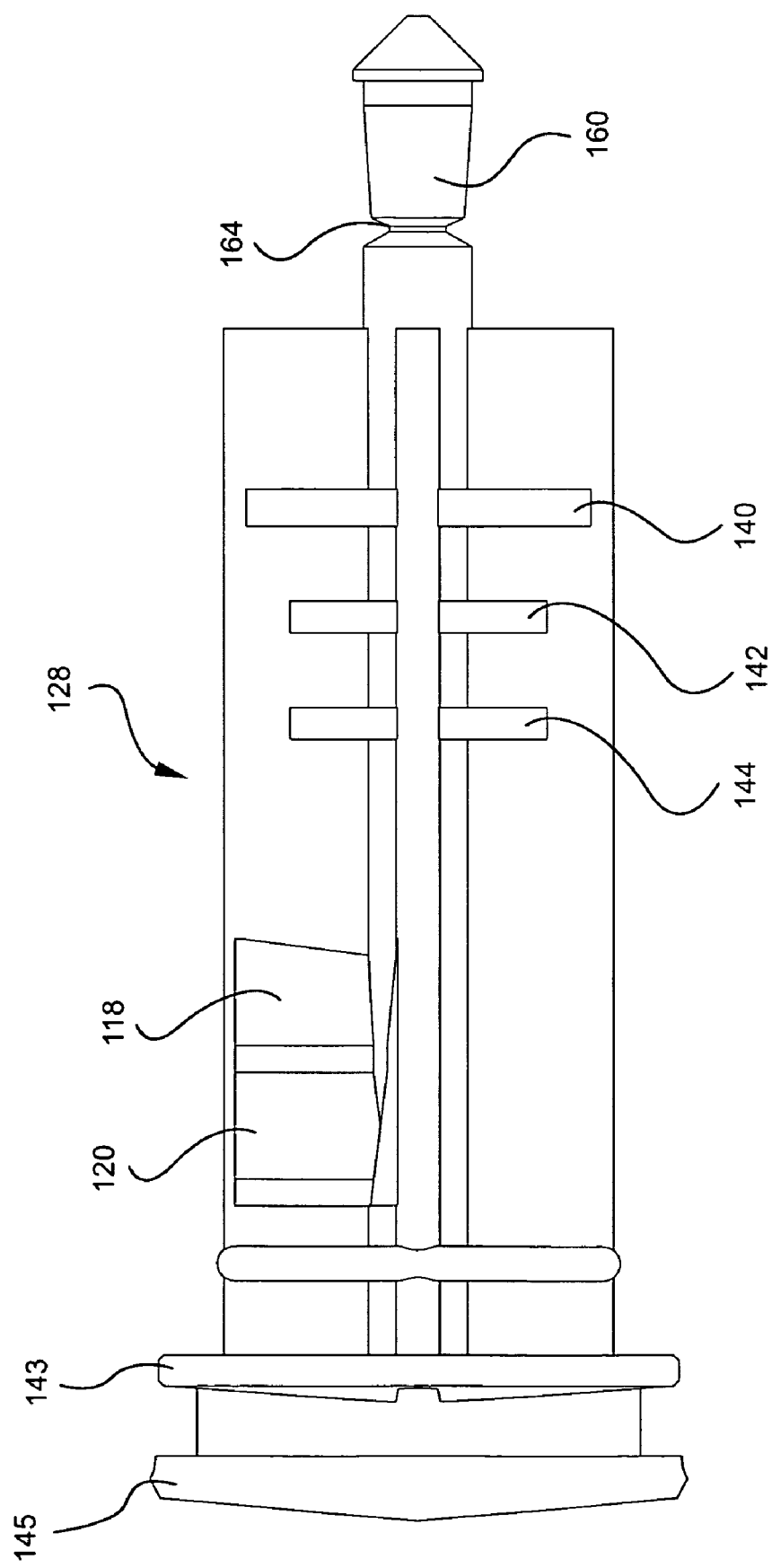
FIG. 3 shows a side elevational view of the stopper shown in FIG. 2A.
Figure 4:
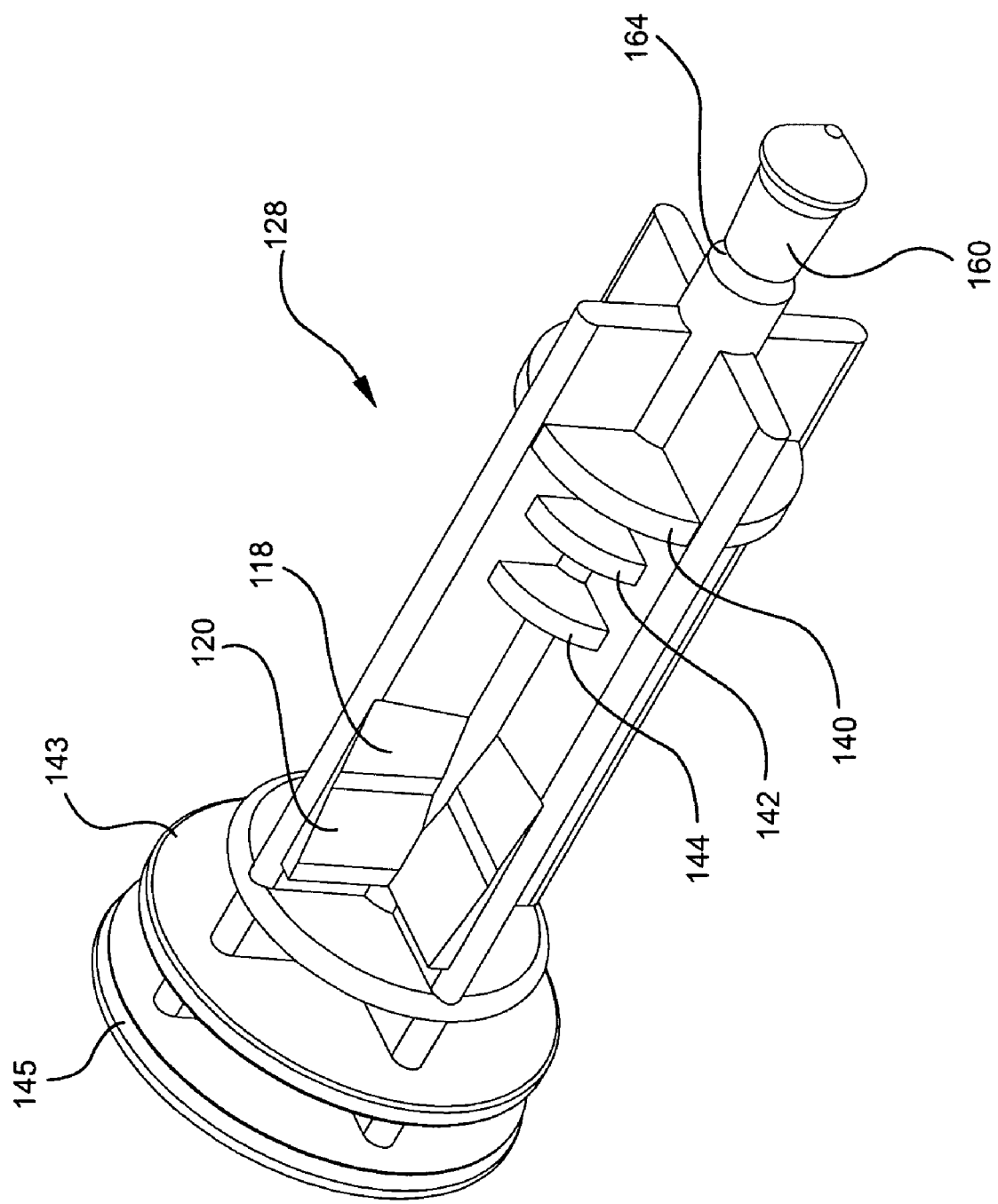
FIG. 4 shows a perspective view of the stopper shown in FIG. 2A.
Figure 5:
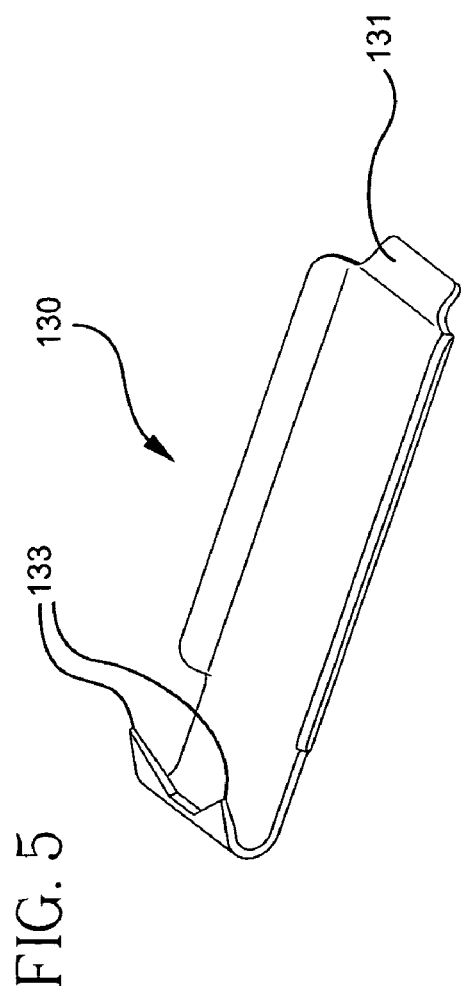
FIG. 5 is a perspective view of the locking element shown in FIG. 2A.
Figure 6:
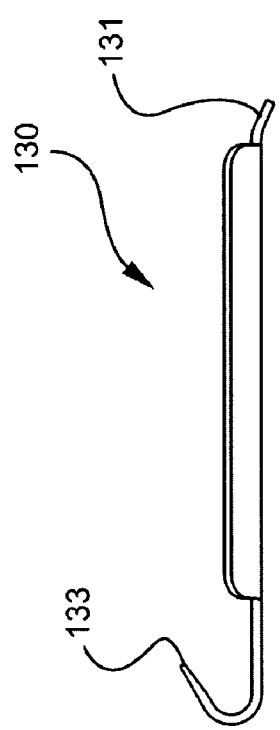
FIG. 6 is a side elevational view of the locking element shown in FIG. 2A.
Figure 7:
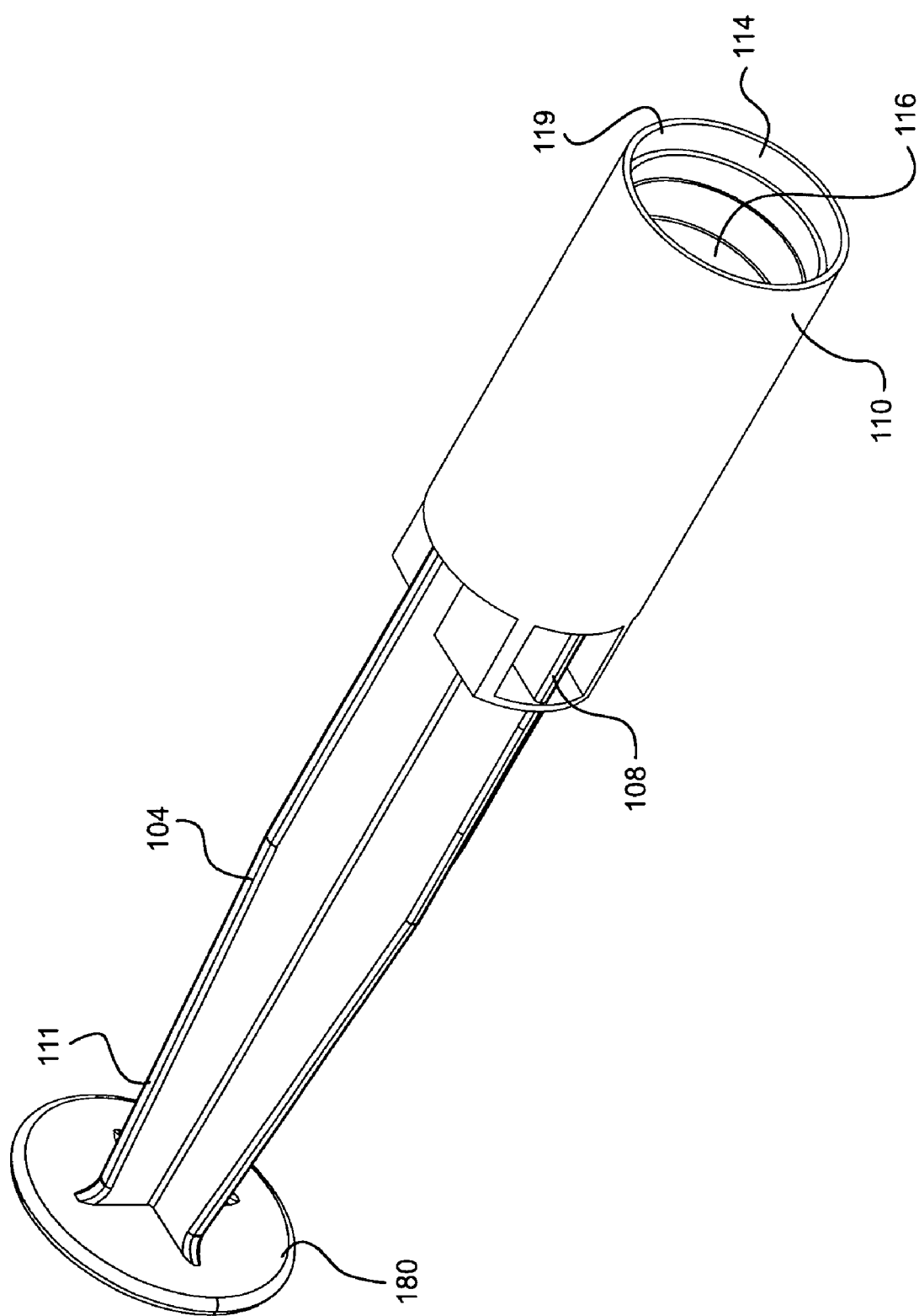
FIG. 7 is a perspective view of the plunger rod shown in FIG. 2A.
Figure 8:
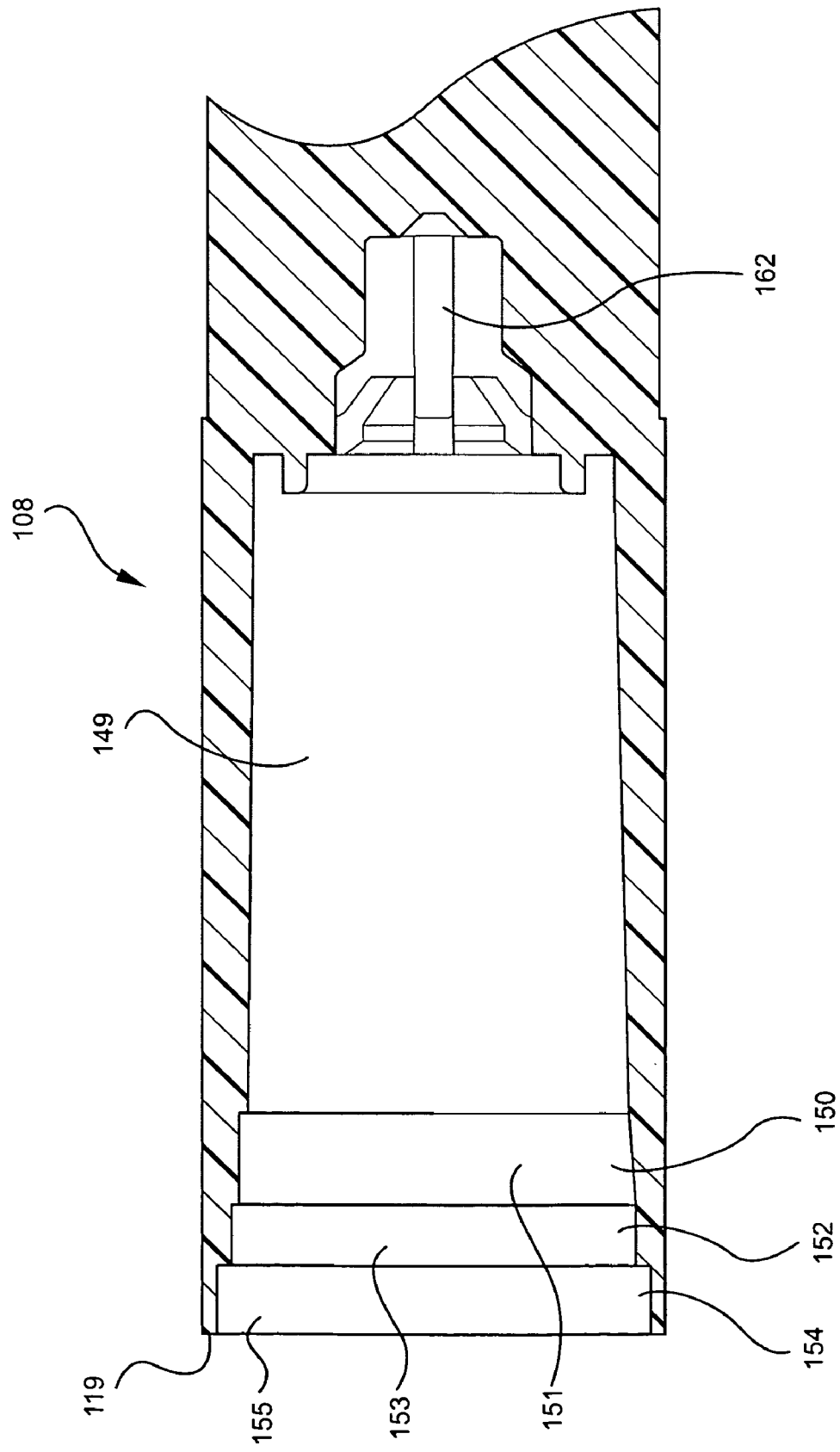
FIG. 8 is an enlarged partial cross-sectional view of a distal portion of the plunger rod according to one or more embodiments.

Before describing several exemplary embodiments of the invention, it is to be understood that the invention is not limited to the details of construction or process steps set forth in the following description. The invention is capable of other embodiments and of being practiced or being carried out in various ways.

Aspects of the present invention are directed to a syringe assembly having a disabling mechanism. According to one or more embodiments of the invention, the disabling mechanism is automatically or passively engaged during use of the syringe assembly. The disabling mechanism permits variable dosages from the syringe assembly and enables a selected number of cycles or strokes by the plunger rod before being automatically disabled. In one specific embodiment, the disabling mechanism provides two aspirating and two dispensing cycles before being automatically disabled. The assembly enables the aspiration and dispensing of a selected volume of a diluent into a vial to reconstitute a drug, pharmaceutical agent, or other substance and then aspirating the reconstituted substance back into the syringe. A selected volume of the reconstituted substance can be injected or delivered to a patient where the volume of the substance that is delivered can be the same or different than the volume of the substance aspirated into the syringe barrel. According to one or more embodiments, the syringe is automatically disabled after the injection or delivery stroke by retracting the plunger rod, which activates the disabling mechanism.

According to one or more embodiments, the disabling mechanism is actuated by the axial movement of the plunger rod with respect to the syringe barrel and to the stopper by moving the plunger rod in the aspirating direction. The stopper is coupled to the plunger rod to allow limited axial movement of the stopper with respect to the plunger rod. The disabling mechanism moves through a series of stages by reversing the direction of the axial movement of the plunger rod with respect to the stopper to move the mechanism in a step-wise manner to the disabling position. The disabling position of the mechanism is attained by the relative movement between the plunger rod and the stopper and is not dependent on the position of the stopper within the syringe barrel or the length of the stroke by the stopper. In this manner, the syringe assembly is able to dispense a desired volume of the drug or other substance, and the disabling mechanism can be actuated after the final dispensing or injection stroke regardless of the position of the stopper in the syringe barrel. By actuating the disabling mechanism, the stopper cannot be retracted to aspirate a substance into the syringe barrel but allows any substance remaining in the syringe barrel to be dispensed.

In this disclosure, a convention is followed wherein the distal end of the device is the end closest to a patient and the proximal end of the device is the end away from the patient and closest to a practitioner.

The syringe assembly according to one or more embodiments of the present invention will now be described with specific reference to FIGS. 1-8. A syringe assembly 100 having a disabling mechanism includes a syringe barrel 102 and a plunger assembly 104. Barrel 102 includes a cylindrical sidewall 106 having an inside surface defining a chamber 109 for retaining fluid, an open proximal end 113 and a distal end 115 including a distal wall 117 having a passageway 105 therethrough in fluid communication with the chamber. In this embodiment, the distal wall of the barrel includes an elongate tip 103 extending distally therefrom and having a passageway in fluid communication with the passageway in the distal wall. In the embodiment shown, barrel 102 also includes a needle cannula 170 having a proximal end 171, a distal end 172 and a lumen 173 therethrough. The proximal end of the needle cannula is attached to elongate tip 103 so that the lumen of the needle cannula is in fluid communication with passageway 105 in the barrel.

Plunger assembly 104 includes an elongate hollow plunger rod 108, a stopper 128 and a locking element 130. Plunger rod 108 includes a proximal end 111, an open distal end 110, a distal lip 119, and an interior surface 116 defining an interior recess 114. The proximal end of the plunger rod 111 includes a thumbpress 180 for application of force to the plunger rod by a user. Flanges 182 may be provided on the barrel for the user to grasp during application of force to the thumbpress 180. Stopper 128 includes a sealing element 145 having a peripheral surface 143 forming a seal with the inside surface of the barrel.

A projection extends proximally from the sealing element 145 and forms a longitudinal recess 129, and there is at least one distal ramp 118 on the longitudinal recess. In the embodiment shown, there are two pairs of distal ramps 118, 120 on the longitudinal recess. The first distal ramp 118 extends in a distal direction to the second distal ramp 120. The longitudinal recess further includes at least one proximal recess detent on the longitudinal recess. In the embodiment shown, three proximal recess detents 140, 142, 144 are shown on the proximal end of the longitudinal recess. The first recess detent 140 located closest to the proximal end is larger than the second recess detent 142, which is larger than the third recess detent 144.

The locking element 130 includes a proximal portion having a proximal edge 131 and a distal portion having an outwardly facing barb 133. In the embodiment shown, there are two outwardly facing barbs 133 on the distal portion of the locking element. When the syringe is assembled, the locking element 130 is positioned in the longitudinal recess so that the barb contacts the interior surface of the plunger rod and the proximal edge contacts the proximal recess detent. The ramps 118, 120 urge the proximal portion and the barbs 133 of the locking element outward so that the barb contacts the interior surface 116 of the hollow plunger rod.

In accordance with one embodiment, the locking element comprises a single unit or single leg. In other embodiments, the locking element may bifurcate into two legs at the proximal edge 131. Further embodiments may also include a single barb or multiple barbs. In yet other embodiments, the length of the locking element may be increased or decreased.

According to one embodiment, the distal end of the hollow plunger rod includes a plurality of plunger rod ramps 150, 152, 154. First plunger rod ramp 150 has an inner diameter that is larger than the inner diameter of the main body 149 of the plunger rod 108. The second ramp 152 has an inner diameter larger than the inner diameter at the first plunger rod ramp, and the third ramp 154 on the distal end of the plunger rod has an inner diameter larger than the second ramp. The first, second and third plunger rod ramps 150, 152, 154 provide respectively first, second and third longitudinally spaced barb rests 151, 153, 155.

As will be appreciated further below, during an aspiration cycle to drawing medicament into the syringe with proximal sliding movement, followed by expulsion of medicament with distal sliding movement of the plunger rod and stopper within the chamber, causes the barbs 133 to extend past the distal lip 119 on the plunger rod toward the inside surface of the barrel, preventing further movement of the plunger rod with respect to the chamber. Distal sliding movement of the plunger rod and stopper causes the distal portion of the locking element to ride up the ramps on the longitudinal recess of the stopper and the barbs of the locking element to move outwardly towards the interior surface of the hollow plunger rod.

The stopper is preferably integrally formed of thermoplastic material such as polyethylene. The sealing element and/or the peripheral sealing surface thereon may be made of elastomeric materials such as thermoplastic elastomers, natural rubber, synthetic rubber and combinations thereof.

In another specific embodiment, the stopper 128 is slidably attached to the distal end of the plunger rod 108 to allow initial relative movement between the plunger rod and the stopper so that the stopper remains stationary when the plunger rod is moved an initiating distance D1 in a proximal direction. This relative motion can be provided by a projecting boss 160 slidably mounted in channel 162 of the plunger rod. A frangible or breakable connection 164 may also be provided to facilitate separation of the stopper from the plunger rod 108, which will be described further below.

Figure 9:
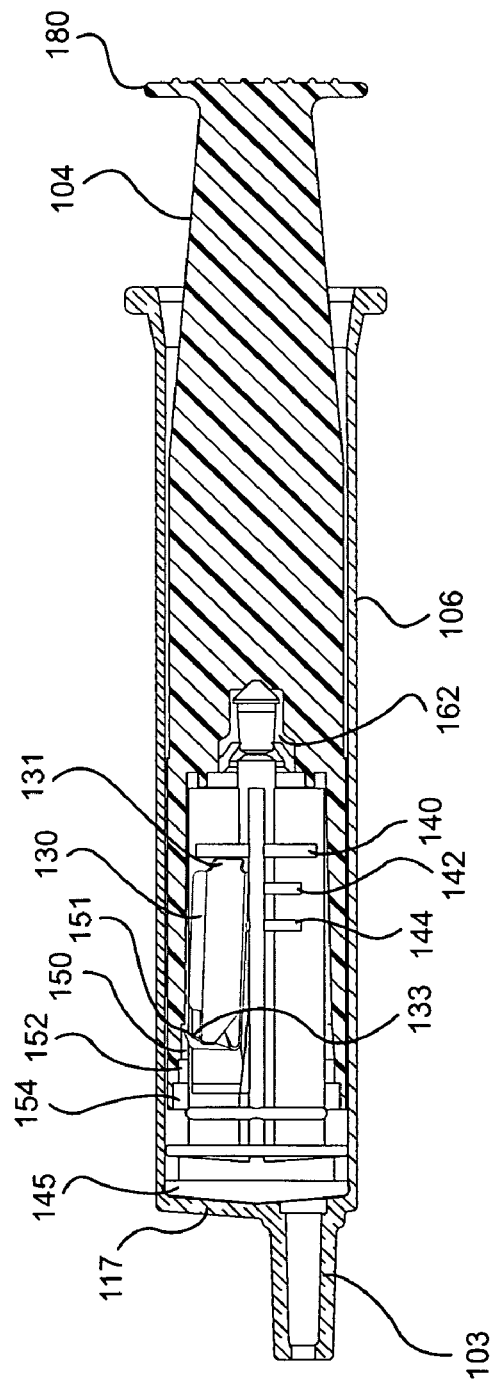
FIG. 9 is a cross-sectional view taken along line 9-9 of FIG. 1.

Operation of the syringe assembly will now be described with specific reference to FIGS. 9-18. As described above, after a user removes the syringe assembly from the package, the components of the syringe assembly would be as shown in FIG. 9. In this position, the stopper and sealing element 145 are bottomed against the distal wall 117 of the syringe. The proximal edge of the locking element 131 is engaged against the first recess detent 140 and the barbs 133 of the locking element 130 are resting upon the first barb rest 151 of the first ramp 150 of the plunger rod.

Figure 10:
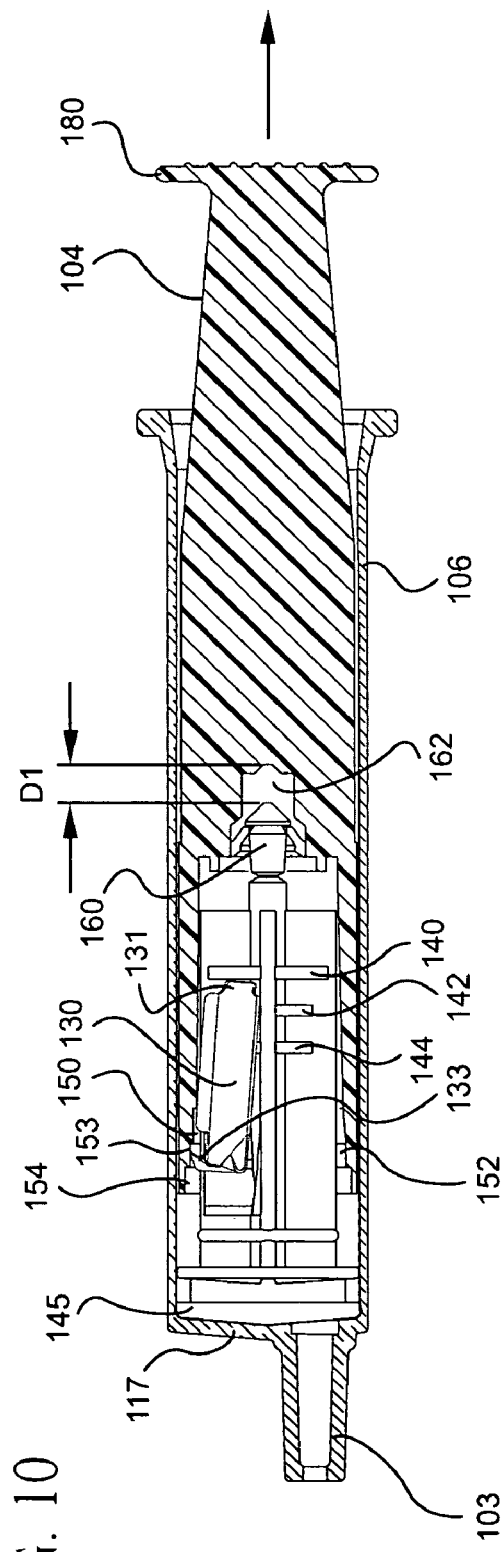
FIG. 10 is an illustration of FIG. 9 after initial proximal movement of the plunger rod.

When a user applies initial proximal force to the plunger rod 108 as indicated by the arrow in FIG. 10, the stopper 128 and sealing element 145 remain stationary while the plunger rod 108 is moved an initiating distance D1 in a proximal direction. The locking element 130 also remains stationary as its proximal edge 131 continues to engage against the first recess detent 140. However, the proximal movement of the plunger rod causes the position of the barb 133 to move from the first barb rest 151 of the first ramp 150 to the second barb rest 153 of the second ramp 152. This relative motion can be provided by a projecting boss 160 slidably mounted in channel 162 of the plunger rod.

In operation of this specific embodiment, further proximal movement of the plunger rod, as indicated by the arrow in FIG. 11, causes the syringe barrel to be filled with a desired amount of fluid. After the plunger rod has moved the initiating distance D1 and the user continues to apply a proximal force to the plunger rod, the stopper 128, sealing element 145, locking element 130 and the plunger rod 108 move together in the proximal direction. The barbs of the locking element 133 continue to rest on the second barb rest 153 of the second ramp 152 and the proximal edge 131 continues to engage with the first recess detent.

After filling the syringe barrel with the desired amount of fluid, when the user applies an initial distal force to the plunger rod 108, as indicated by the arrow in FIG. 12, the plunger rod 108 is moved an initiated distance D1 in a distal direction, while the stopper 128 and sealing element 145 remain stationary due to the relative movement between the stopper and the plunger rod within the channel 162. As the plunger rod moves slidably in the proximal direction, the locking element 130 moves in the distal direction with the plunger rod 108, causing the proximal edge 131 to move from the first recess detent 140 to the second recess detent 142. The barbs of the locking element 133 remain on the second barb rest 153 of the second ramp 152. Further, as the stopper 128 remains stationary while the locking element 130 moves in the proximal direction, the ramp 118 urges the barb 133 outward to the interior surface 116 of the plunger rod.

Further distal movement of the plunger rod 108 causes the sealing element 145 to contact the distal wall of the barrel 117 until the fluid has been expelled from the barrel, as shown in FIG. 13. At completion of this expelling cycle, the barb of the locking element 133 remain resting on the second barb rest 153 of the second ramp 152 and the proximal edge continues to engage with the second recess detent 142.

Still with respect to a specific embodiment, after expulsion of fluid from the syringe, the plunger rod 108 can be moved an initiating distance D1 in a proximal direction, as shown by the arrow in FIG. 14. During this proximal movement, there is initial relative movement between the plunger rod 108 and the stopper 128, so that the stopper 128 remains stationary and the plunger rod 108 moves in the proximal direction causing the position of the barb on the locking element 133 to move from the second barb rest 153 of the second ramp 152 to the third barb rest 155 of the third ramp 154. Further proximal movement of the plunger rod 108 causes movement of the stopper 128, sealing element 145 and the plunger rod 108 in unison in a proximal direction while fluid is drawn into the syringe, as illustrated by FIG. 15. The proximal edge 131 remains on the second recess detent 142.

After fluid is drawn into the syringe, distal movement of the plunger rod 108 for the length of the initiated distance D1 results in the stopper 128 remaining in a fixed position so that there is relative movement between the stopper 128 and the plunger rod 108 within the channel 162, as demonstrated in FIG. 16. Further, the locking element 130 moves in the distal direction with the plunger rod 108 while the second distal ramp 120 exerts a force on the locking element 130 causing it to move outward toward the interior surface of the plunger rod 116. As the locking element 130 moves in the distal direction, the proximal edge 131 moves from the second recess detent 142 to the third recess detent 144.

Thereafter, further distal movement of the plunger rod 108 causes the sealing element 145 to contact the distal wall of the barrel 117 until the fluid has been expelled from the barrel, as illustrated by FIG. 17. If the user attempts to reuse the syringe or otherwise apply a force in the proximal direction to the plunger rod 108, the stopper 128 and locking element 130 remain stationary, while the plunger rod 108 moves proximally for an initiated distance D1 due to the relative movement of the stopper 128 and plunger rod 108 within the chamber 162. As the plunger rod 108 moves past the stopper 128 and locking element 130, the position of the locking element 130 is urged past the distal lip 119 of the plunger rod 108, thereby causing the barb 133 to engage the interior wall of the barrel and locking the plunger rod 108 in the barrel 102.

As shown in FIG. 18, the proximal end of the stopper 128 includes a frangible connection 164 that breaks upon application of proximal force to the plunger rod 108 after the plunger rod has been locked in the barrel 102. In specific embodiments, the proximal end of the stopper 128 includes boss member 160 including the frangible connection 164.

According to an embodiment of the invention, the locking element 130 is made of sheet metal, and the stopper 128 is integrally formed of thermoplastic material. In a specific embodiment, locking element 130 comprises a sheet of material consisting of a single leg. As otherwise mentioned, embodiments of the locking element 130 may also include two or more legs.

As will be appreciated from the foregoing description, embodiments of the invention provide a syringe assembly which permits a variable dose of diluent, chosen by the user at the time of use, to be drawn into the syringe, dispensing the diluent into a vial containing a substance to be reconstituted, drawing a selected amount of the reconstituted substance back into the syringe and then delivering the contents of the syringe. The selected amount of the reconstituted substance may be equal or less than the full volume reconstituted at the discretion of the user. In one or more embodiments, the syringe assembly is automatically disabled after the final injection stroke by reversing the direction of the movement of the plunger rod from the dispensing direction to the aspirating direction. After the injection stroke of the syringe plunger the plunger rod is retracted to activate the disabling mechanism to prevent axial movement of the stopper toward the proximal end of the syringe barrel thereby preventing the stopper from being removed and preventing reuse of the syringe.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A syringe assembly comprising:
    a barrel including a cylindrical side wall having an inside surface defining a chamber for retaining fluid, an open proximal end and a distal end including a distal wall having a passageway therethrough in fluid communication with said chamber;
    an elongate hollow plunger rod having a proximal end, an open distal end, an interior surface, and a distal lip on the distal end of said plunger rod;
    a stopper at the distal end of the plunger rod, the stopper including a sealing element having a peripheral surface forming a seal with said inside surface of the barrel, and a projection extending proximally from the sealing element and forming a longitudinal recess including a distal portion, the longitudinal recess including a plurality of ramps disposed on the distal portion of the longitudinal recess and inclined outwardly in a distal direction and a plurality of proximal recess detents; and
    a locking element including a proximal portion having a proximal edge and a distal portion having an outwardly facing barb, the locking element positioned in the longitudinal recess so that the barb contacts the interior surface of the plunger rod and the proximal edge contacts the proximal recess detent,
    wherein the plurality of ramps and the plurality of proximal recess detents on the longitudinal recess cooperate so that the distal portion of the locking element rides up the plurality of ramps to move the distal portion of the locking element outwardly towards the interior surface of the plunger rod during distal sliding movement of the plunger rod and stopper and proximal sliding movement followed by distal sliding movement of the plunger rod and stopper within the chamber causes the barb to extend past the distal lip on the plunger rod and toward the inside surface of the barrel, preventing further proximal movement of the plunger rod with respect to the chamber.

2. The syringe assembly of claim 1, wherein the distal end of the hollow plunger rod includes a plurality plunger rod ramps complementary to the ramps on the longitudinal recess of the stopper.

3. The syringe assembly of claim 2, wherein the assembly further comprises first, second and third proximal recess detents, first, second and third ramps on the longitudinal recess of the stopper and first, second and third plunger rod ramps, the plunger rod ramps providing first, second and third longitudinally spaced barb rests.

4. The syringe assembly of claim 3, wherein the stopper is slidably attached to the distal end of the plunger rod to allow initial relative movement between the plunger rod and the stopper so that the stopper remains stationary when the plunger rod is moved an initiating distance in a proximal direction, causing the barbs on the locking element to move from the first barb rest to the second barb rest.

5. The syringe assembly of claim 4, wherein further proximal movement of the plunger rod causes the syringe barrel to be filled with a desired amount of fluid.

6. The syringe assembly of claim 5, wherein distal movement of the plunger rod after the syringe barrel has been filled results in the stopper remaining in a fixed position so that there is relative movement between the stopper and the plunger rod causing the barbs to advance to the second barb rest and the proximal edge of the locking element to engage the second proximal recess detent while the second ramp on the longitudinal recess of the stopper urges the barbs toward the interior surface of the plunger rod.

7. The syringe assembly of claim 6, wherein further distal movement of the plunger rod causes the seal to contact the distal wall of the barrel until the fluid has been expelled from the barrel.

8. The syringe assembly of claim 7, wherein the plunger rod is moved an initiating distance in a proximal direction during which there is initial relative movement between the plunger rod and the stopper so that the stopper remains stationary and causing the barbs on the locking element to move from the second barb rest to the third barb rest.

9. The syringe assembly of claim 8, wherein further proximal movement of the plunger rod causes movement of the seal and the plunger rod in a proximal direction while fluid is drawn into the syringe.

10. The syringe assembly of claim 9, wherein distal movement of the plunger rod after drawing fluid into the syringe results in the stopper remaining in a fixed position so that there is relative movement between the stopper and the plunger rod causing the barbs to advance to the third barb rest and the proximal edge of the locking element to engage the third proximal recess detent while the third ramp on the longitudinal recess of the stopper urges the barbs outwardly toward the interior surface of the plunger rod.

11. The syringe assembly of claim 10, wherein further distal movement of the plunger rod causes the seal to contact the distal wall of the barrel until the fluid has been expelled from the barrel and the locking element is urged past the distal lip of the plunger rod and causing the barbs to engage the interior wall of the barrel and locking the plunger rod in the barrel.

12. The syringe assembly of claim 11, wherein the proximal end of the stopper includes a frangible connection that breaks upon application of proximal force to the plunger rod after the plunger rod has been locked in the barrel.

13. The syringe assembly of claim 12, wherein the proximal end of the stopper includes boss member including the frangible connection.

14. The syringe assembly of claim 1 wherein the locking element is made of sheet metal.

15. The syringe assembly of claim 1 wherein the stopper is integrally formed of thermoplastic material.

16. The syringe assembly of claim 1, wherein the locking element comprises a sheet of material consisting of a single leg.

17. The syringe assembly of claim 1, wherein the locking element comprises a single leg and a free proximal edge.

18. A syringe assembly comprising:
- a barrel including a cylindrical side wall having an inside surface defining a chamber for retaining fluid, an open proximal end and a distal end including a distal wall having a passageway therethrough in fluid communication with said chamber;
- an elongate hollow plunger rod having a proximal end, an open distal end, an interior surface, and a distal lip at the distal end of said plunger rod;
- a stopper at the distal end of the plunger rod, the stopper including a sealing element having a peripheral surface forming a seal with said inside surface of the barrel, and a projection extending proximally from the sealing element and forming a longitudinal recess;
- means for locking the plunger rod to the barrel to prevent relative movement of the plunger rod with respect to the barrel after the plunger rod has been moved proximally and then distally for at least one cycle; and
- means for moving the locking element in a distal direction relative to the plunger rod and exerting a force on the distal portion of a locking element disposed within the hollow plunger rod to move the distal portion of the locking element outwardly toward the interior surface of the plunger rod, said means for moving the locking element disposed on the distal portion of the longitudinal recess.

19. A syringe assembly comprising:
- a barrel including a cylindrical side wall having an inside surface defining a chamber for retaining fluid, an open proximal end and a distal end including a distal wall having a passageway therethrough in fluid communication with said chamber;
- an elongate hollow plunger rod having a proximal end, an open distal end, an interior surface, and a distal lip at the distal end of said plunger rod;
- a stopper at the distal end of the plunger rod the stopper including a sealing element having a peripheral surface forming a seal with said inside surface of the barrel, and a projection extending proximally from the sealing element and forming a longitudinal recess, first and second distal ramps on a distal portion of the longitudinal recess and first and second detents on the longitudinal recess; and
- a locking element including a proximal portion having a proximal edge and a distal portion having an outwardly facing point, the locking element positioned in the longitudinal recess so that the distal ramps and the detents on the longitudinal recess cooperate so the distal portion of the locking element rides up at least the first distal ramp to move the distal portion of the locking element outwardly towards the interior surface of the plunger rod and the proximal edge of the locking element retains the locking element in place, wherein proximal sliding movement followed by distal sliding movement of the plunger rod and stopper within the chamber causes the point to extend past the distal lip on the plunger rod and toward the inside surface of the barrel, preventing further movement of the plunger rod with respect to the chamber.

20. The syringe assembly of claim 19, wherein the assembly comprises three distal ramps and three detents on the longitudinal recess and the syringe assembly is operative to allow the plunger rod to be moved proximally and then distally for two cycles to permit aspiration and expulsion of fluid from the syringe barrel.

21. The syringe assembly of claim 20, wherein the stopper is connected to the plunger rod by a frangible connection so that when the point of the locking element is engaged with the chamber, application of proximal force to the plunger rod causes the frangible connection to break.

* * * * *